(12) United States Patent
Topolkaraev

(10) Patent No.: US 6,984,439 B2
(45) Date of Patent: Jan. 10, 2006

(54) RESPONSIVE FILM WITH CORRUGATED MICROLAYERS HAVING IMPROVED PROPERTIES

(75) Inventor: Vasily A. Topolkaraev, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 83 days.

(21) Appl. No.: 10/293,915

(22) Filed: Nov. 12, 2002

(65) Prior Publication Data

US 2004/0091677 A1    May 13, 2004

(51) Int. Cl.
*B32B 3/28* (2006.01)
*A61F 13/15* (2006.01)

(52) U.S. Cl. ............... 428/185; 428/212; 428/913; 604/358; 604/367; 604/378; 604/385.01

(58) Field of Classification Search ............ 428/182, 428/184, 212, 324, 327, 331, 913, 185; 604/358, 604/367, 375, 378, 385.01, 385.14
See application file for complete search history.

(56) References Cited

U.S. PATENT DOCUMENTS

| | | | | |
|---|---|---|---|---|
| 479,999 | A | * | 8/1892 | Thompson ............... 428/183 |
| 520,366 | A | * | 5/1894 | Leaver ................... 428/185 |
| 1,189,140 | A | * | 6/1916 | Lane ..................... 428/154 |
| 2,091,918 | A | * | 8/1937 | Finck .................... 428/182 |
| 2,314,876 | A | * | 3/1943 | Greene ................... 428/34.3 |
| 3,051,453 | A | | 8/1962 | Sluijters |
| 3,576,707 | A | | 4/1971 | Schrenk et al. |
| 4,286,006 | A | * | 8/1981 | Boelter .................. 428/182 |
| 4,604,313 | A | | 8/1986 | McFarland et al. |
| 4,655,757 | A | | 4/1987 | McFarland et al. |
| 4,704,116 | A | | 11/1987 | Enloe |
| 4,724,114 | A | | 2/1988 | McFarland et al. |
| 5,261,899 | A | | 11/1993 | Visscher et al. |
| 5,269,995 | A | | 12/1993 | Ramanathan et al. |
| 5,376,430 | A | | 12/1994 | Swenson et al. |
| 5,462,708 | A | | 10/1995 | Swenson et al. |
| 5,468,428 | A | | 11/1995 | Hanschen et al. |
| 5,486,167 | A | | 1/1996 | Dragoo et al. |
| 5,536,555 | A | | 7/1996 | Zelazoski et al. |
| 5,562,465 | A | | 10/1996 | Taguchi et al. |
| 5,562,650 | A | | 10/1996 | Everett et al. |
| 5,593,399 | A | | 1/1997 | Tanzer et al. |
| 5,667,864 | A | | 9/1997 | Landoll |
| 5,691,034 | A | | 11/1997 | Krueger et al. |
| 5,700,553 | A | | 12/1997 | Cohen et al. |

(Continued)

FOREIGN PATENT DOCUMENTS

EP      0 151 018 A2    8/1985

(Continued)

OTHER PUBLICATIONS

Schrenk et al., "Coextruded Multilayer Polymer Films and Sheets", *Polymer Blends*, vol. 2, Chapter 15, pp. 129-165, Academic Press, Inc., 1978.

(Continued)

*Primary Examiner*—Donald J. Loney
(74) *Attorney, Agent, or Firm*—Brinks Hofer Gilson & Lione; G. Peter Nichols

(57) ABSTRACT

A multi-microlayer thermoplastic film structure and methods of making the same. More specifically, this invention relates to a multi-microlayer film having a plurality of corrugated polymer layers and a plurality of thermoplastic elastomer layers. Filler materials and surfactants may be included in either the corrugated polymer layer or the thermoplastic elastomer layer. The multi-microlayer films may be formed in a co-extrusion process.

37 Claims, 3 Drawing Sheets

U.S. PATENT DOCUMENTS

| | | |
|---|---|---|
| 5,756,039 A | 5/1998 | McFall et al. |
| 5,773,562 A | 6/1998 | Gruber et al. |
| 5,814,178 A | 9/1998 | Jacobs |
| 5,866,173 A | 2/1999 | Reiter et al. |
| 5,873,963 A | 2/1999 | Trombetta et al. |
| 5,938,648 A | 8/1999 | LaVon et al. |
| 5,944,706 A | 8/1999 | Palumbo et al. |
| 6,071,450 A | 6/2000 | Topolkaraev et al. |
| 6,107,538 A | 8/2000 | Young et al. |
| 6,117,438 A | 9/2000 | Topolkaraev et al. |
| 6,231,557 B1 | 5/2001 | Krautkramer et al. |
| 6,258,996 B1 | 7/2001 | Goldman |
| 6,261,674 B1 | 7/2001 | Branham et al. |
| 6,383,960 B1 | 5/2002 | Everett et al. |
| 6,459,514 B2 | 10/2002 | Gilbert et al. |
| 6,475,600 B1 | 11/2002 | Morman et al. |
| 2002/0019187 A1 | 2/2002 | Carroll et al. |
| 2002/0127385 A1 | 9/2002 | Topolkaraev et al. |
| 2002/0165516 A1 | 11/2002 | Datta et al. |
| 2003/0031837 A1 | 2/2003 | Kody et al. |

FOREIGN PATENT DOCUMENTS

| | | |
|---|---|---|
| WO | WO 99/33651 | 7/1999 |
| WO | WO 01/26597 A1 | 4/2001 |

OTHER PUBLICATIONS

Im et al., "Coextruded Microlayer Film and Sheet", *Journal of Plastic Film & Sheeting*, vol. 4, pp. 104-115, Apr. 1988.

Mueller et al., "Novel Structures by Microlayer Coextrusion—Talc-Filled PP, PC/SAN, and HDPE/LLDPE", *Polymer Engineering and Science*, vol. 37, No. 2, pp. 355-362, Feb. 1997.

Mueller et al., "Breathable Polymer Films Produced by the Microlayer Coextrusion Process", *Journal of Applied Polymer Science*, vol. 78, pp. 816-828, 2000.

\* cited by examiner

RESPONSIVE FILM WITH CORRUGATED MICROLAYERS HAVING IMPROVED PROPERTIES

FIELD OF THE INVENTION

The present invention relates, in general, to microlayer film structures, personal care products including these films, and methods of making the same. More specifically, this invention relates to a microlayer film having corrugated microlayers and elastomeric microlayers and channel spaces between the corrugated microlayers and elastomeric microlayers.

BACKGROUND OF THE INVENTION

Disposable absorbent products currently find widespread use in many applications. For example, in the infant and child care areas, diapers and training pants have generally replaced reusable cloth absorbent articles. Other typical disposable absorbent products include feminine care products such as sanitary napkins or tampons, adult incontinence products, and health care products such as surgical drapes or wound dressings. A typical disposable absorbent product generally comprises a composite structure including a liquid-permeable topsheet, a fluid acquisition layer, an absorbent structure, and a liquid-impermeable backsheet. These products usually include some type of fastening system for fitting the product onto the wearer.

Disposable absorbent products are typically subjected to one or more liquid insults, such as of water, urine, menses, or blood, during use. As such, the outer cover materials of the disposable absorbent products are typically made of liquid-insoluble and liquid impermeable materials, such as polypropylene films, that exhibit a sufficient strength and handling capability so that the disposable absorbent product retains its integrity during use by a wearer and does not allow leakage of the liquid insulting the product.

Furthermore, solid waste disposal is becoming an ever increasing concern throughout the world. As landfills continue to fill up, there has been an increased demand for material source reduction in disposable products, the incorporation of more recyclable and/or degradable components in disposable products, and the design of products that may be disposed of by means other than by incorporation into solid waste disposal facilities such as landfills.

As such, there is a need for new materials that may be used in disposable absorbent products that generally retain their integrity and strength during use, but after such use, the materials may be more efficiently disposed of. For example, the disposable absorbent product may be easily and efficiently disposed of by composting.

Additionally, breathability is an important aspect for personal care articles. For example, breathability in a diaper provides significant skin health benefits to the baby wearing the diaper. Moisture vapors are allowed to pass through the outer cover, leaving the baby's skin drier and less prone to diaper rash.

Other important features of films used in personal care products include the opacity, the softness, tactility and drape of the film. Therefore, it is desirable to maximize these properties as well as they may make the film more comfortable when in use and in the manufacture of the personal care product.

It would therefore be beneficial to prepare a breathable, degradable films for personal care products. The degradable films may be used as barrier films in a disposable absorbent product intended for the absorption of fluids such as body fluids. In one embodiment, these films would have increased softness, tactility and drape.

SUMMARY OF THE INVENTION

The present invention is directed to a breathable film material that is easily prepared and readily processable into predetermined final structures.

One aspect of the present invention concerns a breathable film material that includes a microstructure arrangement that includes a plurality of corrugated microlayers, a plurality of corrugated elastomeric layers, and channel spaces between the corrugated microlayers and the elastomeric layers.

The corrugated microlayers, or the elastomeric layers, or both, may be biodegradable. Both or only one of the corrugated microlayers and the elastomeric layers may contain a particulate filler material which, upon stretching, may provide porosity initiating sites to enhance the breathability of the film.

The film materials of the present invention may be used as a component for a personal care product. Additionally, these materials are highly breathable, which makes the materials more comfortable to the wearer of the laminate. Also, the films are softer, more tactile and more drapable than prior art films. The films also include void spaces and microlayer corrugations that makes the films extensible and allows the films to absorb, retain and transport fluids. Finally, the films are relatively simple to produce as they are composed of a plurality of microlayers.

The film materials of the present invention are useful in a wide variety of personal care articles, such as diapers, adult incontinence products, training pants, and feminine care products, among others.

The present invention provides a film having a plurality of corrugated microlayers and a plurality of elastomeric microlayers. The present invention also provides a nanoscale microlayer assembly of the multi-microlayer hybrid films which offer significant breathability while providing barrier protection against fluids with improved softness, comfort, tactility, drapability, opacity and stretch.

The present invention is directed to a polymer film comprising a plurality of coextruded microlayers including a layer comprising an elastomeric, melt-extrudable polymer and a layer comprising a melt-extrudable polymer capable of forming the corrugated microlayers. The multi-microlayer film of this invention has sufficient strength and breathability for elastomeric use in applications such as disposable absorbent personal care products, garments, and other covering materials.

One advantage of the multi-microlayer films of the present invention is that they offer a significant improvement in breathability, softness, tactility, drapeability, opacity, fluid management, and extensibility over the prior art multi-layer films. The use of a plurality of microlayers enables films to be produced which permit water vapor produced by an individual to pass through the film and into the atmosphere. The corrugations in the microlayers provide void spaces that may absorb, retain and transport fluids. This enables the skin to stay drier and makes the film more comfortable to wear while helping to improve skin wellness.

Additionally, these films are designed to provide a high barrier against liquid penetration through the film. The microlayer polymer film of this invention is particularly suitable for making personal care items such as diapers, feminine care products, adult incontinence products, and training pants, and health care products such as wound dressings or surgical gowns where a unique combination of one or more film-functional attributes such as softness, high opacity, fluid retention, fluid distribution, elastomeric behavior, water-response, low noise and breathability are desired.

More particularly, the multi-microlayer polymer film of this invention includes a plurality of layers comprising the elastomeric, melt-extrudable polymer and a plurality of corrugated layers comprising the melt-extrudable polymer. The plurality of elastomeric layers and plurality of corrugated layers are arranged in a series of parallel repeating laminate units, each laminate unit comprising at least one of the elastomeric layers and at least one of the corrugated layers.

Generally, the individual microlayers of the film of this invention have a thickness small enough so that the elastomeric layers and the corrugated layers of the microlayer film adhere to one another to form a laminate. Each microlayer in the polymer film of this invention has a thickness from about 0.1 micron to about 150 microns. In another embodiment, each microlayer has a thickness that does not exceed about 100 microns. In another embodiment each microlayer has a thickness that does not exceed about 50 microns. In yet another embodiment, each microlayer has a thickness which is not less than about 0.5 microns. In still another embodiment each microlayer has a thickness that is not less than about 1 micron.

Broadly described, the film of this invention has corrugated and elastomeric layers totaling about 5 to about 100 in number, and in an alternative embodiment about 16 to about 60 in number.

According to a particular embodiment of the present invention, each microlayer of the multi-microlayer film may include a void spaces in the form of channels in each microlayer due to corrugations in each microlayer. These void spaces may be used for modifying or enhancing properties of the microlayer film, such as improved fluid retention and distribution.

According to another aspect of this invention, a method for making a multi-microlayer polymer film is provided. This method includes coextruding an elastomeric, melt-extrudable polymer and a degradable or non-degradable, melt-extrudable polymer to form a laminate comprising an elastomeric layer including the elastomeric, melt-extrudable polymer and a layer including a melt-extrudable polymer capable of forming the corrugated microlayers. The method further includes separating the laminate while the laminate is in a melt-extrudable state to form a pair of laminate halves each including a portion of the elastomeric layer and a portion of the second polymer layer having the melt-extrudable polymer capable of forming the corrugated microlayers. After separation, the laminate halves are thinned and widened and then stacked on top of one another to reform the laminate so that the laminate comprises a plurality of repeating laminate units in parallel stacking arrangement. Each laminate unit comprises an elastomeric layer including the elastomeric, melt-extrudable polymer and a second polymer layer including the melt-extrudable polymer. The steps of separating, thinning and widening, and stacking are repeated to form the laminate into the multi-microlayer polymer film. Other methods to form multi-microlayer films known in the prior art may also be employed to form a plurality of repeating laminate units in parallel stacking arrangement. (See W. J. Schrenk and T. Ashley, Jr., "Coextruded Multilayer Polymer Films and Sheets, *Polymer Blends*", Vol. 2, Academic Press, New York (1978)). The resulting microlayer film may also be stretched uniaxially or biaxially and thinned to partially delaminate the elastomeric layers from the second polymer layer to thereby produce corrugations in the second polymer layer when the film is relaxed. The stretching may also reduce the basis weight of the microlayer film, enhance access of water and other aqueous liquids into the laminate structure of the microlayer film, enhance disintegration of the microlayer film in water, and enhance the water vapor transport rate or breathability of the film. Additionally, a second corrugated space may be generated in each elastomeric layer to enhance the overall properties of the films.

The corrugated layer structure caused by stretching and partial delamination may create a "spacer layer effect" that reduces dampness on the outside of the laminate when used as an outercover of an absorbent garment.

The films of the invention may be breathable and demonstrate a dramatically improved softness and drape, improved extensibility, and a reduced noisiness. The film may also provide three-dimensional profiles, needed for visual appeal and/or improved bonding and lamination. A large void volume in the form of channels in the corrugated layers and elastomer layers may provide improvement in opacity, thermal insulation property, fluid distribution and other benefits such as void space for absorbed fluids.

Performance characteristics of the film with corrugated microlayers may include one or more of the following, such as soft hand/silky feel, improved drape, improved opacity, extremely low noisiness, moisture and fluids wicking/absorption, breathability, controllable bonding temperatures, extensibility and elastic recovery, good printability, and a formation of three-dimensional profiles and structures beneficial for skin wellness. Fine particulate fillers and superabsorbent particles, and dyes may be easily incorporated into the film structure. Polymeric components may be selected to provide an improved biodegradation of the film. The film with corrugated microlayers may be used in feminine care products, diapers, personal health care products, medical products and various absorbent articles.

DETAILED DESCRIPTION OF THE INVENTION

Figure 1:
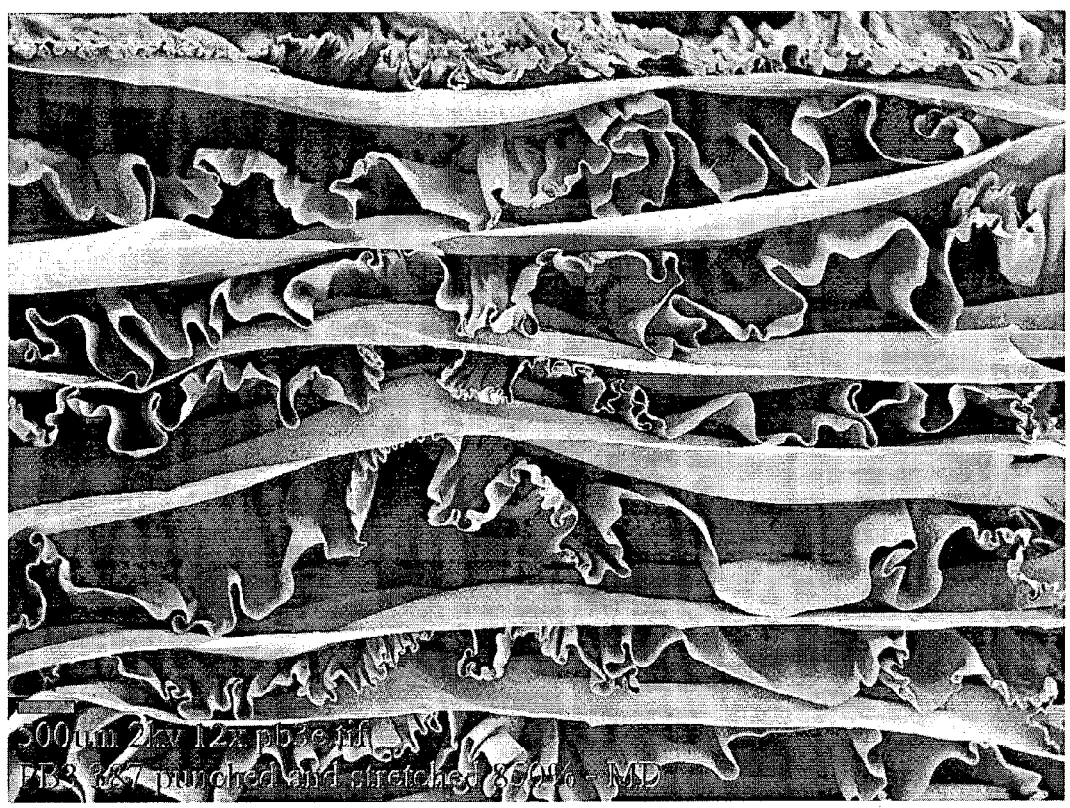
FIG. 1 is a scanning electron microscopy (SEM) micrograph, taken at a magnification of 12×, showing a representative cross-sectional view in machine direction of a corrugated-microlayer film of the invention.

The present invention encompasses a multi-microlayer polymer film that has sufficient elasticity, strength and breathability for use in applications such as absorbent personal care products. Below is a detailed description of embodiments of this invention including a method for coextruding the microlayer polymer film, followed by a description of uses and properties of the film and particular examples of the film.

The present invention is directed to films with corrugated microlayers and precursor films, which are made by coextrusion of alternating layers of thermoplastic, melt extrudable elastomer and melt extrudable stretchable thermoplastic polymer. The films of the present invention may have corrugated microlayers in the melt extrudable elastomer layers, the melt extrudable stretchable thermoplastic polymer layers, or both. At least one of the corrugated microlayers will generally include layers composed of a thermoplastic melt extrudable non-elastomeric polymer. Suitable thermoplastic polymers for use in this invention are stretchable in a solid state and, if required, at elevated temperature to allow a drawing and thinning of layers during film stretching. Stretching at elevated temperature may be applied to enhance stretchability.

This invention includes novel hybrid multi-microlayer films composed of a multi-microlayer assembly of corrugated microlayers and microlayers of thermoplastic elastomers (TPE), which may also be corrugated. By definition, "multi-microlayer" means a film having a plurality of alternating layers wherein, based upon the process by which the film is made, each microlayer becomes partially integrated or adhered with the layers above and below the microlayer. This is in contrast to "multi-layer" films wherein a conventional co-extruded film-making equipment forms a film having only a few layers and wherein each layer is separate and distinct from each other layer. Additionally, during formation of the films of the present invention, which may include stretching, the microlayers will partially delaminate from one another, thereby permitting the corrugations to be formed upon relaxation or activation of the film. However, partial integration or adherence of layers remains, unlike multi-layer films. The partial integration of the layers also increases the breathability, softness, tactility, and drapability of the film.

This invention discloses a novel-film with a microstructure, which includes a plurality of corrugated microlayers, a plurality of elastomeric layers, which may also be corrugated in a cross-direction to the corrugated microlayers, and channel spaces between the corrugated microlayers and elastomer layers. Corrugated microlayers, or elastomer layers, or both may be biodegradable. Both corrugated microlayers and elastomer microlayers may contain particulate filler material, which upon stretching of the film may provide porosity initiating sites. The film with corrugated microlayers may include a third microlayer of a melt processible polymer, which is located between the corrugated microlayer and an elastomeric layer. The third microlayer may include filler particles and may provide for controlled delamination and corrugation of layers.

The multi-microlayer polymer film of this invention comprises a plurality of coextruded microlayers which form a laminate structure. The coextruded microlayers include a plurality of elastomeric layers comprising a first polymer comprising an elastomeric, melt-extrudable polymer and a plurality of layers comprising a second polymer comprising a degradable or non-degradable melt-extrudable polymer capable of forming corrugated microlayers. The plurality of elastomeric layers and plurality of the second polymer layer including the melt-extrudable polymer capable of forming corrugated microlayers are arranged in a series of parallel repeating laminate units. Each laminate unit comprises at least one of the second polymer layers and at least one of the elastomeric layers. Desirably, each laminate unit has one second polymer layer laminated to an elastomeric layer so that the coextruded microlayers alternate between second polymer and elastomeric polymer. Then, after stretching and releasing of the film, corrugations form in the second polymer layer, the elastomeric layer, or both. These corrugations produce channels having void spaces between the corrugated and elastomeric layers. Activation using heat or microwave energy might be used to form corrugations in the stretched film.

Alternatively, each laminate unit may also include a third layer, a tie or transition layer, between the corrugated layer and the elastomeric layer. The tie layer is useful for modifying or enhancing properties of the microlayer film such as softness, opacity, fluid absorption and retention. This tie layer may also control debonding/delaminating between the elastomeric and corrugated layers thus controlling the frequency and the amplitude of corrugations. The tie layer may be formed from a filled thermoplastic polymer and may include a variety of melt extrudable polymers. The third layer may be formed from thermoplastic water soluble or swellable polymers or superabsorbent materials, for example, the third layer may be formed from thermoplastic, melt extrudable polyethylene oxide resin or melt extrudable polyvinyl alcohol resin. Particular composition of the tie layer depends on the elastic and second polymer used to form the laminate units.

The corrugating layer functions such that, during film stretching, the layer is plastically drawn and thinned. When a stretching force is released, the layer is partially debonded from the elastomeric layers and forms corrugations under a contraction force provided by the stretched elastomer layers. The buckling phenomenon and a formation of corrugations and folds in the drawn thermoplastic layer, which is confined between the contracting elastomer layers, is a fundamental mechanism for the formation of the film with corrugated microlayers. Drawability and a sufficient stiffness to allow buckling and the formation of corrugations is a characteristic for the polymeric component of corrugating microlayer. The polymer that forms the corrugating microlayers may be wettable. This may increase the wicking property of the film.

During the formation of corrugated microlayers the multilayer film changes dimensions in the direction of stretching and in z-direction (thickness direction). Typically it shrinks in the stretch direction and expands in z-direction (thickness) providing three-dimensional profiles and structures. Additionally, during this formation, the elastomeric layer may also form corrugations, but generally the channels formed will be in a direction substantially perpendicular to the channels formed in the melt-extrudable polymer capable of forming corrugated microlayers.

Each microlayer in the polymer film of this invention has a thickness from about 0.1 micron to about 150 microns. In another embodiment, each microlayer has a thickness that does not exceed about 100 microns. In another embodiment each microlayer has a thickness that does not exceed about 50 microns. More particularly, each microlayer has a thickness that is not less than 0.5 microns. In still another embodiment, each microlayer has a thickness that is not less than about 1 micron. In still another embodiment, the microlayers of the film have a thickness from about 0.5 microns to about 100 microns. Microlayers, however, form laminate films with high integrity and strength because they do not substantially delaminate after microlayer coextrusion due to the partial integration or strong adhesion. However, the corrugated microlayers will be partially delaminated from the elastomeric layers upon formation of the corrugated layers as described previously and below. Microlayers enable combinations of two or more layers of normally incompatible polymers into a monolithic film with a strong coupling between individual layers without using compatibilizing agents. However, compatibilizing agents may still be used to enhance the properties of the multi-microlayer films of the present invention. The term "monolithic film" as used herein means a film that has multiple layers which adhere to one another and function as a single unit.

The number of microlayers in the film of this invention vary broadly from about 5 to about 100 in number, and in another embodiment from about 16 to about 60 in number. However, based upon the thickness of each microlayer, the number of microlayers in the film is determined by the desired overall film thickness. In one embodiment, the multi-microlayer hybrid films, prior to stretching, have a thickness of from about 1 to about 100 mils. In another embodiment, the films, prior to stretching, have a thickness of from about 2 to about 50 mils. In yet another embodiment, the films, prior to stretching, have a thickness of from about 2 to about 20 mils. In another embodiment, the films, after stretching and multilayer corrugations, have a thickness of from about 3 to about 1000 mils. In still another embodiment, the films, after stretching and multilayer corrugations, have a thickness of from about 10 to about 500 mils. In still another embodiment, the films, after stretching and multilayer corrugations, have a thickness of from about 20 to about 250 mils. 1 mil is equal to $1/1000$ of an inch.

The term "melt-extrudable polymer" as used herein means a thermoplastic material having a melt flow rate (MFR) value of not less than about 0.2 grams/10 minutes, based on ASTM D1238. More particularly, the MFR value of suitable melt-extrudable polymers ranges from about 0.2 g/10 minutes to about 100 g/10 minutes. In another embodiment, the MFR value of suitable melt-extrudable polymers ranges from about 0.5 g/10 minutes to about 50 g/10 minutes. In yet another embodiment the MFR value ranges from about 5 g/10 minutes to about 50 g/10 minutes to provide desired levels of process ability.

Still more particularly, suitable melt-extrudable thermoplastic polymers for use in this invention are stretchable in solid state to allow a stretch processing of the multi-microlayered film. Stretching in solid state means stretching at a temperature below the melting point of the thermoplastic polymer. Stretching of the film reduces film thickness and may create porosity, thereby increasing the water vapor transport rate of the film and, hence, breathability. The ratio of true tensile fracture stress (tensile force at failure divided by the cross-sectional area of the failed specimen), and the stress at yielding, is useful to determine the stretchability of the polymer film. In one embodiment, such ratio for suitable melt-extrudable polymers used in this invention ranges from about 1 to about 150, more particularly from about 5 to about 100, and even more particularly from about 10 to about 50.

The thermoplastic elastomer microlayers of the film of this invention are desirably composed of a thermoplastic, melt extrudable polymer. The elastomeric means that the polymer may be stretched to several hundred % of elongation and may recover to about its original length when the stretching force is removed. The function of elastomeric layers is to provide a confinement and a sufficient contraction force to corrugating microlayers after the precursor multilayer film is stretched to a specified draw ratio and a stretching force is released. As used herein, a "precursor multiplayer film" is a film that has been formed, but not yet stretched. As such, a precursor multiplayer film has alternating microlayers of the melt extrudable elastomer polymer and the melt extrudable stretchable thermoplastic polymer. Corrugation of microlayers may be enhanced using activation by heat or microwave energy.

Suitable elastomeric materials that may be used for the elastomeric component of the multi-microlayer film include a melt extrudable thermoplastic elastomer such as a polyurethane elastomer, a copolyether ester, a polyether block polyamide copolymer, an ethylene vinyl acetate (EVA) elastomer, a styrenic block copolymer, an olefinic elastomer, as well as other elastomers known to those skilled in the polymer art. Useful elastomeric resins include polyester polyurethane and polyether polyurethane. Examples of two commercially available elastomeric resins are sold under the trade designations PN 3429-219 and PS 370-200 MORTHANE® polyurethanes. MORTHANE® is a registered trademark of Huntsman Polyurethanes having an office in Chicago, Ill. 60606. Another suitable elastomeric material is ESTANE® polyurethane, a registered trademark of Noveon, Inc. having an office in Cleveland, Ohio 44141. Still another suitable elastomeric material is PEARLTHANE® polyurethane, a registered trademark of Merquinsa having an office in Boxford, Mass. 01921.

Three additional elastomeric materials include a polyether block polyamide copolymer which is commercially available in various grades under the trade designation PEBAX®. PEBAX® is a registered trademark of Atofina Chemicals, Inc. having an office in Birdsboro, Pa. 19508. A second elastomeric materials is a copolyether-ester sold under the trade designation ARNITEL®. ARNITEL® is a registered trademark of DSM having an office at Het Overloon 1, NL-6411 TE Heerlen, Netherlands. The third elastomeric material is a copolyether-ester sold under the trade designation HYTREL®. HYTREL® is a registered trademark of E.I. DuPont de Nemours having an office in Wilmington, Del. 19898.

The elastomeric component may also be formed from a styrenic block copolymer such as KRATON®. KRATON® is a registered trademark of Kraton Polymers having an office in Houston, Tex.

The elastomeric component may further be formed from a biodegradable elastomeric material such as polyester aliphatic polyurethanes or polyhydroxyalkanoates.

The elastomeric component may be formed from an olefinic elastomeric resin, such as elastomers and plastomers including single-site catalyzed or metallocene catalyzed polyethylene, polypropylene and other alpha-olefin homopolymers and copolymers, having density less than about 0.89 grams/cc. One such plastomer is an ethylene-based resins and/or polymers sold under the trade designation AFFINITY®. AFFINITY® is a registered trademark of Dow Chemical Company having an office in Freeport, Tex. AFFINITY® resin is an elastomeric copolymer of ethylene and octene produced using Dow Chemical Company's INSITE™ constrained geometry catalyst technology. Another plastomer is sold under the trade designation EXACT® which includes single-site catalysts derived copolymers and terpolymers. EXACT® is a registered trademark of Exxon Mobile Corporation having an office in Irving, Tex. Other suitable olefinic elastomers that may be used include also polypropylene-derived elastomers.

The elastomeric polymer may include surface-modifying end groups such as, e.g., polydimethylsiloxane end groups or other functional groups. The end groups, which are covalently bonded, may reduce surface tension of elastomer microlayers, and may control interaction between the elastomer layers and corrugating layers. The polyurethanes with surface-modified end groups may be obtained from the Polymer Technology Group, Inc., a business having offices in Berkeley, Calif.

The corrugated microlayers of the film of this invention may include a thermoplastic non-elastomer polymer component that may be biodegradable or non biodegradable, or combinations, blends or mixtures thereof. The thermoplastic non-elastomer polymer should be melt-extrudable so that the polymer may be coextruded along with the elastomeric polymer to form the microlayer film. In addition, the elastomer polymer component and/or the thermoplastic non-elastomer polymer component may be permeable to water vapor when in the form of a film. Finally, the thermoplastic non-elastomer polymer component polymer is selected such that the polymer is capable of being formed into a corrugated layer. By "capable of being formed into a corrugated layer" it is meant that after the thermoplastic non-elastomer polymer and elastomeric polymer are coextruded, stretching of the coextruded film will cause the thermoplastic non-elastomer polymer to partially debond from the elastomeric layer such that when the stretching force is removed, the elastomeric polymer recovers more of its original shape than the thermoplastic non-elastomer polymer component layer, thereby causing corrugations to form in the thermoplastic non-elastomer polymer component layers.

Suitable biologically degradable polymers are characterized by being degraded in the presence of naturally occurring microorganisms such that the films break down into smaller pieces or loses strength significantly, such that if the film is placed in a biologically-active environment, for example composting and sludge digestion, the film will be broken down. Biologically degradable polymers useful in the present invention include, but are not limited to, biodegradable aliphatic polyesters, polymers and copolymers of polycaprolactone, polymers and copolymers of polylactic acid (PLA), polymers and copolymers of polybutylene succinate, poly(butylene succinate-adipate), other biodegradable melt extrudable polymers and copolymers, and blends and mixtures thereof.

Biodegradable resins useful for this invention include also aliphatic-aromatic co-polyesters sold under the trade designation EastarBio™, a registered trademark of Eastman Chemical Company having an office in Kingsport, Tenn. 37662. Another aliphatic-aromatic co-polyester is sold under the trade designation Ecoflex®, a registered trademark of BASF Corporation having an office in Mount Olive, N.J. 07828. Still another useful biodegradable resin is thermoplastic polyesteramide available from Baer Corporation having an office in Pittsburgh, Pa. Polylactic acid polymers and copolymers useful for this invention are melt-stable, semi-crystalline resins having weight average molecular weight from about 50,000 g/mol to about 200,000 g/mol. These polymers are disclosed in Gruber et al, Melt-Stable Semi-Crystalline Lactide Polymer Film and Process for Manufacture Thereof, U.S. Pat. No. 5,773,562, assigned to Cargill Incorporated, which is herein incorporated by reference. An examples of commercially available PLA resins include Lacty® from Shimadzu Corporation, Lacea® from Mitsui Chemicals, NatureWorks™ PLA from Cargil Dow LLC having office in Minnetonka, Minn. 55343, or L5000 and L9000 from Biomer, having office in D-82151 Krailling, Germany. When using polylactic acid it is preferred that the PLA is in the semi-crystalline form. Still another biodegradable resins include polyhydroxyalkanoates of varying composition and structure, and copolymers, mixtures and blends of foregoing polymers.

The biodegradable polymer or non-biodegradable polymer may include plasticizers, surfactants, solid-state modifiers, processing aids, and other additives to improve melt processability, reduce viscosity, enhance drawability/ stretchability in a solid state, and improve surface properties and thermal stability. Surfactants and additives may also improve wettability and interactions with fluids. In addition, grafting, copolymerization, and modification of end groups may be used to modify the surface properties of the corrugating microlayers and their interaction with elastomeric layers. Among biodegradable polymers, the polymers and copolymers of PLA are desired for this invention because of their stiffness, plasticization potential and ability to accept fillers, good processability, wettability, biodegradation, and other beneficial characteristics. Stretchability of PLA polymers and copolymers may be significantly improved when PLA is stretched above its glass transition temperature.

Non-biodegradable, melt extrudable and stretchable component for corrugating microlayer may be formed from polyolefins, a polyester, a polyether, its copolymers, or blends and mixtures thereof. Examples of non-biodegradable, melt extrudable and stretchable polymers may include polypropylene and its copolymers, polyethylene and its copolymers, and blends and mixtures thereof. Other melt extrudable, stretchable and non-elastomeric polymers may be also useful for this invention as a component for corrugating microlayer. Non-biodegradable polymers may also include plasticizers, surfactants and other additives which may modify and improve the performance and processability of the film. A specific example includes polypropylene resin H 702-35NA obtained from Dow Chemical Company having an office in Midland, Mich. 48674. Polypropylene is useful in the present invention as a non-biodegradable polymer due to its stiffness, good processability, ability to accept fillers and stretchability.

The multi-microlayer films suitably include between about 20% to about 90% of elastomeric resin and from about 80% to about 10% of thermoplastic non-elastomer resin. In another embodiment, the multi-microlayer films suitably include between about 30% to about 70% of elastomeric resin and from about 70% to about 30% of thermoplastic non-elastomer resin. In still another embodiment, the multi-microlayer films suitably include between about 50% to about 70% of elastomeric resin and from about 50% to about 30% of thermoplastic non-elastomer resin.

The microlayer films of the present invention provide one or more of the following advantages. These films may be softer, more drapable, more opaque, and better at adsorbing and transporting fluids. These characteristics are shown in the physical parameters of the films. For example, films of the present invention are thicker than prior art films due to the corrugations. Increased thickness and void spaces between corrugated layers reduce noise, increase opacity, improve thermal insulation properties, and make the films softer. Additionally, these films have a higher void volume in a form of oriented continuous channels formed by microlayer corrugations, thereby increasing the amount of fluid that may be absorbed and/or distributed. In addition, these films are extensible up to 100% elongation and may retract to about its original length when the extension force is removed. Finally, these films have dramatically reduced tensile and shear modulus versus prior art films.

In general, the films of the present invention have a reduced tensile and shear modulus. In one embodiment, the films, before stretching and/or activation, have a tensile modulus range in the machine direction of from about 50 Mpa to about 800 Mpa. In another embodiment, the films, before stretching and/or activation, have a tensile modulus range in the machine direction of from about 100 Mpa to about 500 Mpa. The films with corrugated microlayers, after stretching and/or activation, generally will have a tensile modulus range in the machine direction of from about 0.2 Mpa to about 50 Mpa. In an alternative embodiment, the films with corrugated microlayers, after stretching and/or activation, generally will have a tensile modulus range in the machine direction of from about 0.3 Mpa to about 20 Mpa. In yet another embodiment, the films with corrugated microlayers, after stretching and/or activation, generally will have a tensile modulus range in the machine direction of from about 0.5 Mpa to about 5 Mpa.

In general, the corrugated microlayer film of the present invention may have extensibility in machine direction, in cross direction or in both directions of up to 50% elongation and may retract to about its original length after the removal of an extension force. In another embodiment, the corrugated microlayer film of the present invention may have extensibility in machine direction, in cross direction or in both directions of up to 100% elongation and may retract to about its original length after the removal of an extension force.

The films of the present invention also have an increased void volume and significantly reduced bulk density, which results from microlayer corrugations and void spaces between corrugated microlayers. In one embodiment, the corrugated-microlayer films of the present invention show an increase in void volume of from about 500% to about 5000% relative to the volume of precursor unstretched films. In another embodiment, the corrugated-microlayer films of the present invention show an increase in void volume of from about 1000% to about 3000% relative to the volume of precursor unstretched films. The bulk density of the corrugated-microlayer films of the present invention may be less than about 0.5 grams per cubic centimeter. In another embodiment the bulk density of the corrugated-microlayer films of the present invention may be less than about 0.1 grams per cubic centimeter. In still another embodiment the bulk density of the corrugated-microlayer films of the present invention may be less than about 0.05 grams per cubic centimeter. In still another embodiment the bulk density of the corrugated-microlayer films of the present invention may be less than about 0.03 grams per cubic centimeter.

The films of the present invention also have an increased breathability. The breathability of the multi-microlayer film with corrugated microlayers is expressed as water vapor transmission rate (WVTR). The WVTR is a function of film thickness, multi-microlayer composition, amount of stretch and layer corrugations. In one embodiment, the corrugated multi-microlayer film may deliver breathability normalized to the film thickness in a range of about 500 g mil/day/m$^2$ to about 25,000 g mil/day/m$^2$. In another embodiment, the corrugated multi-microlayer film may deliver breathability normalized to the film thickness in a range of about 1000 g mil/day/m$^2$ to about 20,000 g mil/day/m$^2$ using the Mocon WVTR test procedure. Normalization to the thickness is accomplished by multiplying the measured breathability of the film by the film thickness measured in mils. A suitable technique for determining the WVTR value of a film of the invention is the test procedure standardized by INDA (Association of the Nonwoven Fabrick Industry), number IST-70.4-99 which is incorporated by reference herein. The testing device which may be used for WVTR measurement is known as the Permatran-W Model 100K manufactured by Mocon/Modern Controls, Inc., business having an office in Minneapolis, Minn.

The corrugated microlayers may also include processing additives and solid-state performance modifiers blended with the polymer forming the corrugated microlayers in amounts from about 0.05 up to 30 parts of additive to 100 parts of polymer resin. Suitable additives include a wide variety of materials such as surfactants, mineral acids, halogens, gelatin, adipic acid, metal halides, metal salts, polymeric acids, benzoic acid derivatives, glycol derivatives, phosphoric acid derivatives and sorbitan derivatives. The various additives may have a plasticizing affect, improve melt flow characteristics, improve strength and toughness, improve modulus, modify crystalline structure, and control release properties. Examples of suitable additives include polyethylene oxide, and polyethylene glycol. Antioxidants and ultraviolet stabilizers may also be added to improve oxidative stability and stability to UV light.

In an alternative embodiment, a third component layer may be present in the film. This third component layer may modify the adhesion between an elastomer layer and a stretchable non-elastomer layer, may provide response to fluids and other environments, may prevent migration of plasticizers or other additives from one component layer to another, and may otherwise beneficially modify properties of the film with corrugating microlayers. Suitable polymers for the third component depend on the particular polymers used for the corrugated layer and the elastomeric layer, but generally include filled polyolefins, thermoplastic polyesters, polyalkane-poly(ethylene oxide) block copolymers, filled polyester resins, polyethers, block copolymers of polyesters and polyethers, polyolefin block copolymers, ethylene vinyl acetate copolymers, and blends and mixtures thereof. The third layer may be also formed from thermoplastic water soluble or swellable polymers, or superabsorbent materials; for example, the third layer may be formed from thermoplastic, melt extrudable polyethylene oxide resin or melt extrudable polyvinyl alcohol resin.

Both the corrugated and elastomeric microlayers may include a supplemental material such as a filler material, a surfactant, or other surface active material. The filler material may be a particulate filler material to enhance water vapor permeability of the film, thereby further increasing the breathability of the film. Particulate filler material creates discontinuity in the microlayers to provide pathways for water vapor to move through the film. Particulate filler material may also enhance the ability of the microlayer film to absorb or immobilize fluid, enhance biodegradation of the film, provide porosity-initiating debonding sites to enhance the formation of pores when the microlayer film is stretched, improve processability of the microlayer film and reduce production cost of the microlayer film. In addition, lubricating and release agents may facilitate the formation of microvoids and the development of a porous structure in the film during stretching of the film and may reduce adhesion and friction at filler-resin interface. Surface active materials such as surfactants coated on the filler material may reduce the surface energy of the film, increase hydrophilicity of the film, reduce film stickiness, provide lubrication, or reduce the coefficient of friction of the film.

Suitable filler materials may be organic or inorganic, and are desirably in a form of individual, discreet particles. Suitable inorganic filler materials include metal oxides, metal hydroxides, metal carbonates, metal sulfates, various kinds of clay, silica, alumina, powdered metals, glass microspheres, or vugular void-containing particles. Particularly suitable filler materials include calcium carbonate, barium sulfate, sodium carbonate, magnesium carbonate, magnesium sulfate, barium carbonate, kaolin, carbon, calcium oxide, magnesium oxide, aluminum hydroxide, and titanium dioxide. Still other inorganic fillers may include those with particles having higher aspect ratios such as talc, mica and wollastonite. Suitable organic filler materials include, for example, latex particles, particles of thermoplastic elastomers, pulp powders, wood powders, cellulose derivatives, chitin, chitozan powder, powders of highly crystalline, high melting polymers, beads of highly crosslinked polymers, organosilicone powders, and powders or particles of super absorbent polymers, such as polyacrylic acid and the like, as well as combinations and derivatives thereof. Particles of super absorbent polymers or other superabsorbent materials may provide for fluid immobilization within the corrugated-microlayer film These filler materials may improve toughness, softness, opacity, vapor transport rate (breathability), biodegradability, fluid immobilization and absorption, skin wellness, and other beneficial attributes of the microlayer film.

The particulate filler material is suitably present in the microlayer film in an amount from about 0.5 to about 70% by weight of the film. In one embodiment, the average particle size of the filler material does not exceed about 200 microns. In another embodiment, the average particle size of the filler does not exceed about 50 microns. In still another embodiment, the average particle size of the filler does not exceed about 5 microns. In yet another embodiment, the average particle size of the filler does not exceed about 1 micron.

Suitable commercially available filler materials include the following:

1. SUPERMITE®, an ultrafine ground $CaCO_3$, which is available from Imerys of Atlanta, Ga. This material has a top cut particle size of about 8 microns and a mean particle size of about 1 micron and may be coated with a surfactant, such as Dow Corning 193 surfactant, before mixing with the polymer.

2. SUPERCOAT®, a coated ultrafine ground $CaCO_3$, which is available from Imerys of Atlanta, Ga. This material has a top cut particle size of about 8 microns and a mean particle size of about 1 micron.

3. OMYACARB® UF, high purity, ultrafine, wet ground $CaCO_3$, which is available from OMYA, Inc., of Proctor, Vt. This material has a top cut particle size of about 4 microns and an average particle size of about 0.7 microns and provides good processability. This filler may also be coated with a surfactant such as Dow Corning 193 surfactant before mixing with the polymer.

4. OMYACARB® UFT $CaCO_3$, an ultrafine pigment surface coated with stearic acid, available from OMYA, Inc. This material has a top cut particle size of about 4 microns and a mean particle size of about 0.7 microns and provides good processability.

The filler may also include superabsorbent particles such as finely ground polyacrylic acid or other superabsorbent particles. The superabsorbent filler in the film with corrugated microlayers may provide absorption of fluids and may expand into the void spaces provided by the corrugating microlayers and improve fluid wetting, fluid retention, fluid absorption and distribution properties.

Surfactants may increase the hydrophilicity and wettability of the film, and enhance the water vapor permeability of the film, and may improve filler dispersion in the polymer. For example, surfactant or the surface active material may be blended with the polymers forming elastomer layers and corrugating layers or otherwise incorporated onto the particulate filler material before the filler material is mixed with the elastomeric polymer or the corrugated polymer. Suitable surfactants or surface active materials may have a hydrophile-lipophile balance (HLB) number from about 6 to about 18. Desirably, the HLB number of the surface active material or a surfactant ranges from about 8 to about 16, and more desirably ranges from about 12 to about 15 to enable corrugated-microlayer wettability by aqueous fluids. When the HLB number is too low, the wettability may be insufficient and when the HLB number is too high, the surface active material may have insufficient adhesion to the polymer matrix of elastomeric layer and/or non-elastomer layer, and may be too easily washed away during use. The surfactant modification, or treatment of the microlayer film of the invention or the components of the microlayer film of the invention may provide a water contact angle of less than 90 degrees for the precursor film or corrugated microlayer film or both. Preferably surfactant modification may provide a water contact angle of less that 70 degrees for the precursor film or the corrugated microlayer film of the invention. For example, incorporation of the Dow Corning 193 surfactant into the film components may provide a water contact angle of about 40 degrees. A number of commercially available surfactants may be found in *McMcutcheon's* Vol. 2; Functional Materials, 1995.

Suitable surfactants and surface-active materials for blending with the polymeric components of the microlayer film or treating the particulate filler material include silicone glycol copolymers, ethylene glycol oligomers, acrylic acid, hydrogen-bonded complexes, carboxylated alcohol, ethoxylates, various ethoxylated alcohols, ethoxylated alkyl phenols, ethoxylated fatty esters, stearic acid, behenic acid, and the like, as well as combinations thereof. Suitable commercially available surfactants include the following:

1. Surfactants composed of ethoxylated alkyl phenols, such as Igepal RC-620, RC-630, CA-620, 630, 720, CO-530, 610, 630, 660, 710, and 730, which are available from Rhone-Poulenc, Inc. of Cranbury, N.J.

2. Surfactants composed of silicone glycol copolymers, such as Dow Corning D190, D193, FF400, and D1315, available from Dow Corning of Midland, Mich.

3. Surfactants composed of ethoxylated mono and diglycerides, such as Mazol® 80 MGK, Masil® SF 19, and Mazol® 165 C, available from PPG Industries of Gurnee, Ill.

4. Surfactants composed of ethoxylated alcohols, such as Genapol 26-L-98N, Genapol 26-L60N, and Genapol 26-L-5 which are available from Hoechst Celanese Corporation of Charlotte, N.C.

5. Surfactants composed of carboxylated alcohol ethoxylates, such as Marlowet 4700 and Marlowet 4703, which are available from Huls America, Inc. of Piscataway, N.J.

6. Ethoxylated fatty esters, such as Pationic 138C, Pationic 122A, Pationic SSL, which are available from R.I.T.A. Corporation of Woodstock, Ill.

The surface activate material is suitably present in the respective microlayer in an amount from about 0.5 to about 20% by weight of the microlayer. Even more particularly, the surface active material is present in the respective microlayer in an amount from about 1 to about 15% by weight of the microlayer, and more particularly in an amount from about 2 to about 10% by weight of the microlayer. The surface activate material may be suitably present on the particulate in an amount of from about 1 to about 12% by weight of the filler material. The surfactant or surface active material may be blended with suitable polymers to form a concentrate. The concentrate may be mixed or blended with polymers forming the elastomeric layers, the corrugated layers or both.

The films of the present invention may be made by using two materials having sufficiently different recovery percentages such that after stretching, the microlayers will form corrugations after release of the stretching force. As used herein, "recovery percentage" is defined as the percentage by which the film returns to its original shape. Accordingly, a film having a recovery percentage of 100 will return to its original shape and a film having a recovery percentage of 0 will not recover any of its post-stretched shape.

In one embodiment of the present invention, the film comprises microlayers of an first polymer that has a first recovery percentage. The film also includes second polymer microlayers having a second recovery percentage. The first recovery percentage is in a range of about 30 to about 90%. The second recovery percentage is in a range of from about 10 to about 50%. The first recovery percentage should be higher than the second recovery percentage such that after stretching, partial delamination and recovery, the second polymer microlayers will recover less of their original shape and as the first polymer recovers, the extra material will form corrugations in the second polymer microlayers. As the difference in the recovery percentages increases, more material will be formed in the corrugated layer and as the difference in the recovery percentages decreases, less material will be formed in the corrugated layer. Activating of the film, using heat or microwave energy, may be used to further enhance the degree of recovery of the first polymer and/or the second polymer.

The corrugations are formed by application of a stretching force and then recovery of the first polymer having the higher first recovery percentage. The corrugations in the second polymer layer will be in the machine direction relative to the stretching force, thereby forming channels in the cross direction. Additionally, corrugations may be formed in the first, more elastomeric microlayers. However, these corrugations will be in a cross-direction relative to the stretching force, thereby forming channels in the machine direction.

The corrugations in the films will generally be created by stretching and recovery of the microlayer films. However, the corrugations may also be formed by activating the stretched multi-microlayer film. Activation may be done using an activating force, such as heat, electromagnetic radiation or humidity, depending on the materials used and the desired degree of corrugations in the postprocessed film.

The films with corrugated microlayers may be postprocessed to stabilize the film structure. The post processing may be done by a thermal point or pattern bonding, by embossing, by sealing edges of the film using heat or ultrasonic energy, or by other operations known in the art. One or more nonwoven webs may be laminated to the film with corrugated microlayers to improve strength of the film, its tactile properties, appearance, or other beneficial properties of the film. The nonwoven webs may be spunbond webs, meltblown webs, bonded carded webs, airlaid or wetlaid webs, or other nonwoven webs known in the art.

The films may also be perforated before stretching or after stretching. The perforations may provide z-directional channels for fluid access, absorption and transport, and may improve vapor transport rate. They may also facilitate or modify corrugation of layers by creating strain-intensive sites around perforated channels. Perforation may be accomplished by punching holes using pins of varying diameter, density, and configuration, which may be arranged into a pattern desired for a specific application of the film. The pins to punch holes and perforate the film may be optionally heated. Other methods known in the art may be also used to perforate the film; for example, high speed and intensity water jets, high intensity laser beams, or vacuum aperture techniques may be used to generate a desired pattern of holes in the film of the invention. The holes or perforation channels may penetrate through the entire thickness of the film or may partially perforate the film to a specified channel depth.

As shown in FIG. 1, the film comprises fine corrugated microlayers confined between elastomer layers. FIG. 1 illustrates a typical cross-sectional view in machine direction of the film of the invention. Corrugations in non-elastomer layers are formed in machine direction of the film and are confined between elastomer layers. A plurality of tubular channels formed by microlayer corrugations is oriented in cross direction of the film. These tubular channels provide capillary void spaces for fluids absorption and wicking in cross direction of the film.

Amplitude of the corrugation may be as low as about 5 microns and as large as about 5 millimeters, preferably the amplitude of corrugations may be as low as about 10 microns and as large as about 500 hundred microns. The width of channels formed by layer corrugations may range from about 1 micron to about 10 millimeters, desirably the width of the channels formed by layer corrugations ranges from about 5 microns to about 5 millimeters. In another embodiment, the width of the channels ranges from about 10 microns to about 500 microns and in yet another embodiment the width of channels ranges from about 20 microns to about 250 microns. The corrugated microlayers form void channels of a tubular shape across the width of the film. When corrugated microlayers are wetted, these tubular channels provide capillary void spaces for fluids absorption and wicking. The frequency of crimps or corrugations in the corrugated microlayers may be in the range of about 1 to about 10,000 per 10 millimeter of the film length. In another embodiment, the frequency of crimps or corrugations ranges from about 2 to about 2000 per 10 millimeter of the film length, and even in still another embodiment the frequency of crimps or corrugations ranges from about 20 to about 1000 per 10 millimeter of the film length. The amplitude and frequency of crimps in corrugated microlayers may be affected by one or more of the following factors: stiffness of the corrugating microlayers, thickness of the precursor film, thickness of the microlayers, a contraction force of the expanded elastomer layers, number of layers, and/or bonding and interaction between the layers. For example, the frequency of crimps may be increased and the amplitude of corrugations may be reduced by increasing the number of microlayers or reducing the precursor film thickness. The precursor films with smaller thickness and larger number of layers will also provide smaller channel width. The precursor films having larger thickness and smaller number of layers may provide larger channels and the increased amplitude of the microlayer corrugations The film with corrugated microlayers may be designed to provide a response to different environments. A response means that the film may form corrugating microlayers and shrink in one or two directions and significantly expand in a third direction when exposed to, e.g., mechanical forces, such as stretching, shearing or bending. Heat or microwaves may also activate the film. The multilayer film may be heated between about 60° C. to about 120° C. The amount of heat used for activation depends on the specific materials used to manufacture the film.

To allow the response to shearing or bending, an interaction between the corrugating layers and the elastomer layers is desirably strong enough to prevent a delaminating during initial stretching; however, when intensive bending, stretching and shearing forces are applied, a partial delaminating of the microlayers may be initiated. As a result, the film may shrink in stretch direction and may expand in the z-direction (increase thickness) with the formation of corrugating microlayers. The interaction between the layers may be controlled and tailored by, e.g., the number of layers, surface properties of microlayers, thickness of the microlayers, composition of the layers, and/or filler addition.

Figure 2:
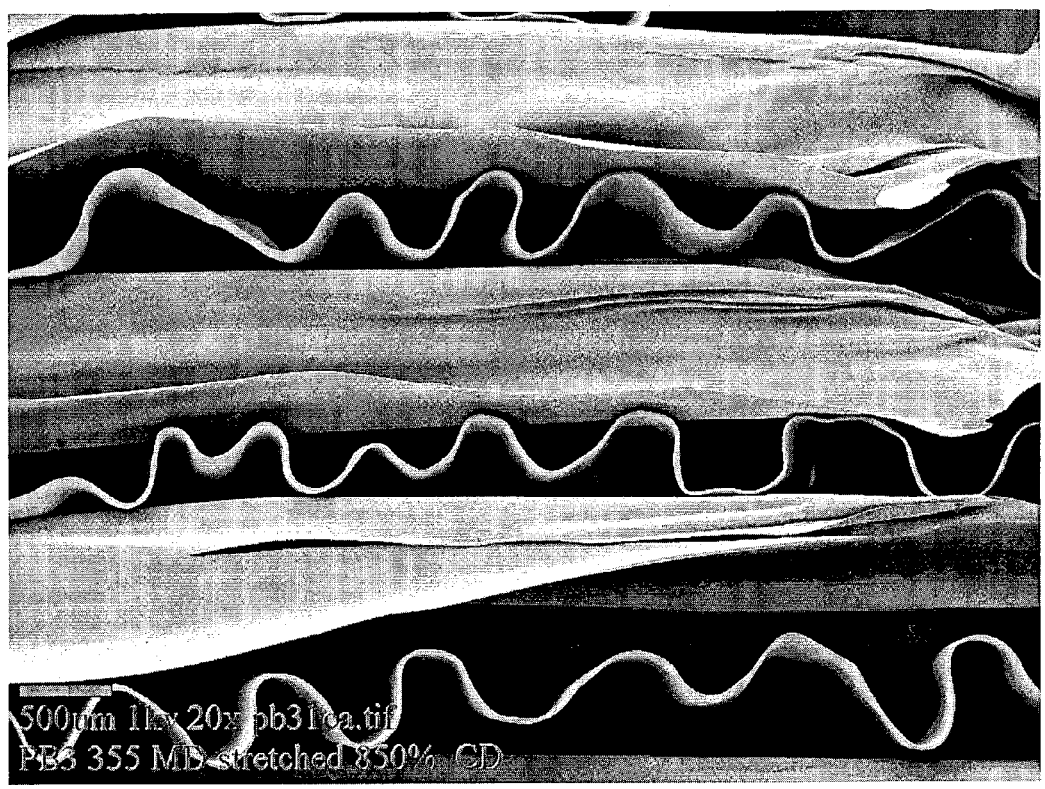
FIG. 2 is a scanning electron microscopy (SEM) micrograph, taken at a magnification of 20×, showing a representative cross-sectional view in cross direction of a corrugated-microlayer film of the invention.

The elastomeric layers may also be corrugated in the cross direction. The tubular shape channels formed by these elastomer-layer corrugations run along the length of the film and are oriented along the machine direction. FIG. 2 illustrates the typical cross-sectional view in cross direction of the film of the invention with elastomer layers corrugated in cross direction and a fine tubular channels formed by these corrugations oriented along the machine direction of the film. These tubular channels provide capillary void spaces for fluids absorption and wicking in machine direction of the film.

The wettable corrugated-microlayer films of the invention may convey by capillary action water or other aqueous fluids through the film in machine direction, in cross direction, or in both directions. The height of vertical wicking may range from about 10 mm to about 200 millimeters. In another embodiment, the height of a vertical wicking may range from about 20 mm to about 150 millimeters. In still another embodiment, the height of a vertical wicking may range from about 40 mm to about 100 millimeters.

Shape memory polymers activatable by heat, radio freaquency waves, or microwaves may be used as an elastomeric component of the film. When the film is stretched, the latent deformation is preserved in shape-memory elastomer layers. Heat or microwaves may activate this deformation and elastomer-layers contraction. As a result, microlayer corrugation and a significant expansion in the z-direction (film thickness) may be achieved by using heat or microwave activation. An examples of a shape memory elastomer includes Pebax® 2533 resin. The amount of heat used for activation depends on the specific materials used, and the stretched multilayer film may be heated between about 60° C. to about 120° C.

The film may be also designed to provide a change in dimensions when exposed to high humidity environment, moisture and/or body fluids. Several designing options exist to allow such a response. For example, a third thin layer of a water-soluble or swellable polymer may be coextruded between a corrugating layer and an elastomer layer. When the stretched multilayer film is exposed to fluids, this fluid-sensitive layer may swell, reduce bonding between the elastomer layer and corrugating layer, and may initiate a layer delaminating and a microlayer corrugation. Examples of such third layer may include layers formed from melt extrudable polyethylene oxide or melt extrudable polyvinyl alcohol resins.

The elastomer layer may be also designed to allow a response to fluids. Grafting or end-group modification may provide an elastomer with hydrophilic or hydrophobic surfaces depending on environment. In one embodiment, the elastomer is water vapor permeable. When the stretched precursor film is exposed to fluids, the surface tension at the layer interfaces may be affected. This may result in a modulation of interaction between the layers, microlayer delaminating and corrugating, and film shrinkage. The elastomeric, segmented block polyurethanes with the functional end groups such as, e.g., polydimethylsiloxane groups are available from the Polymer Technology Group, the business having offices in Berkeley, Calif.

Figure 3:
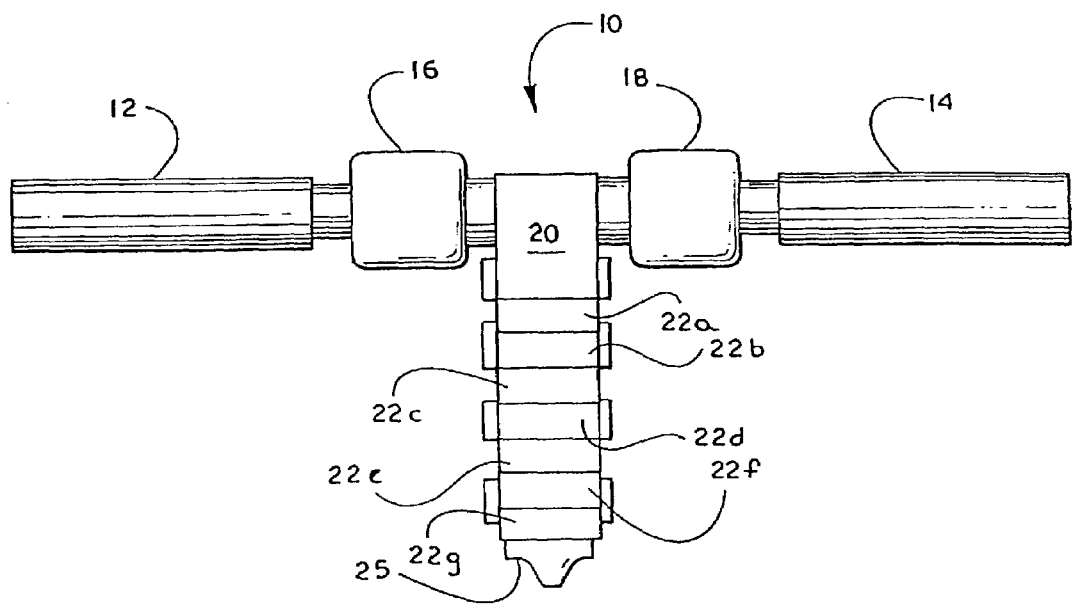
FIG. 3 is a plan view of a coextrusion system for making a microlayer polymer film in accordance with an embodiment of this invention.

A suitable method for making the microlayer film of this invention is a microlayer coextrusion process wherein two or more polymers are coextruded to form a laminate with two or more layers, which laminate is then manipulated to multiply the number of layers in the film. FIG. 3 illustrates a coextrusion device 10 for forming microlayer films. This device includes a pair of opposed single-screw extruders 12 and 14 connected through respective metering pumps 16 and 18 to a coextrusion block 20. A plurality of multiplying elements 22a–g extend in series from the coextrusion block perpendicularly to the single-screw extruders 12 and 14. Each of the multiplying elements includes a die element 24 disposed in the melt flow passageway of the coextrusion device. The last multiplying element 22g is attached to a discharge nozzle 25 through which the final product extrudes. While single-screw extruders are shown, the present invention may also use twin-screw extruders to form the films of the present invention.

Figure 4:
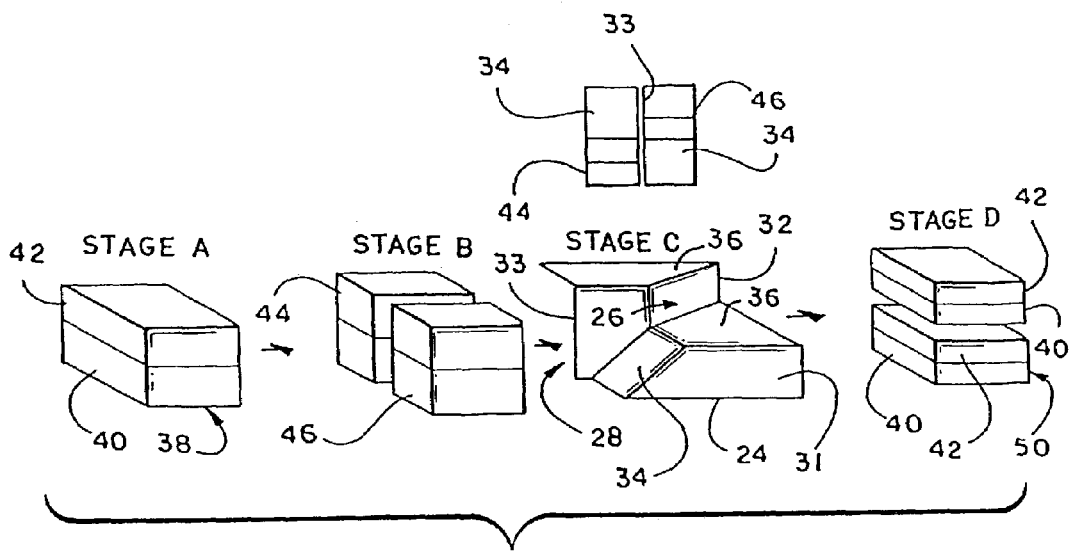
FIG. 4 is a schematic diagram illustrating a multiplying die element and the multiplying process used in the coextrusion system illustrated in FIG. 3.

A schematic diagram of the coextrusion process carried out by the coextrusion device 10 is illustrated in FIG. 4. FIG. 4 also illustrates the structure of the die element 24 disposed in each of the multiplying elements 22a–g. Each die element 24 divides the melt flow passage into two passages 26 and 28 with adjacent blocks 31 and 32 separated by a dividing wall 33. Each of the blocks 31 and 32 includes a ramp 34 and an expansion platform 36. The ramps 34 of the respective die element blocks 31 and 32 slope from opposite sides of the melt flow passage toward the center of the melt flow passage. The expansion platforms 36 extend from the ramps 34 on top of one another.

To make a corrugated microlayer film using the coextrusion device 10 illustrated in FIG. 3, an elastomeric resin is extruded through the first single screw extruder 12 into the coextrusion block 20. Likewise, a thermoplastic polymer, such as polylactic acid or polypropylene, is extruded through the second single screw extruder 14 into the same coextrusion block 20. In the coextrusion block 20, a two-layer melt laminate structure 38 such as that illustrated at stage A in FIG. 4 is formed with the thermoplastic polymer forming a layer on top of a layer of elastomeric polymer. The melt laminate is then extruded through the series of multiplying elements 22a–g to form a multi-layer microlaminate with the layers alternating between the polymer to be corrugated and the elastomeric polymer. As the two-layer melt laminate is extruded through the first multiplying element 22a, the dividing wall 33 of the die element 24 splits the melt laminate 38 into two halves 44 and 46 each having a layer of polymer to be corrugated 40 and a layer of elastomeric polymer 42. This is illustrated at stage B in FIG. 4. As the melt laminate 38 is split, each of the halves 44 and 46 are forced along the respective ramps 34 and out of the die element 24 along the respective expansion platforms 36. This reconfiguration of the melt laminate is illustrated at stage C in FIG. 4. When the melt laminate 38 exits from the die element 24, the expansion platform 36 positions the split halves 44 and 46 on top of one another to form a four-layer melt laminate 50 having, in parallel stacking arrangement, an elastomeric layer, a layer to be corrugated, an elastomeric layer and a layer to be corrugated in laminate form. This process is repeated as the melt laminate proceeds through each of the multiplying elements 22b–g. When the melt laminate is discharged through the discharge nozzle 25, the melt laminate forms a film having from about 4 to about 100 microlayers, depending on the number of multiplying elements.

The foregoing microlayer coextrusion device and process is described in more detail in an article Mueller et al., entitled Novel Structures By Microlayer Extrusion-Talc-Filled PP, PC/SAN, and HDPE-LLDPE, Polymer Engineering and Science, Vol. 37, No. 2, 1997. A similar process is described in U.S. Pat. No. 3,576,707 and U.S. Pat. No. 3,051,453, the disclosures of which are expressly incorporated herein by reference. Other processes known in the art to form multi-microlayer film may also be employed, e.g., coextrusion processes described in W. J. Schrenk and T. Ashley, Jr., "*Coextruded Multilayer Polymer Films and Sheets, Polymer Blends*", Vol. 2, Academic Press, N.Y. (1978).

The relative thickness of the layers to be corrugated and elastomeric layers of the film made by the foregoing process may be controlled by varying the feed ratio of the polymers into the extruders, thus controlling the constituent volume fraction. In addition, one or more extruders may be added to the coextrusion device to increase the number of different polymers in the microlayer film. For example, a third extruder may be added to add a tie layer to the film.

The microlayer film may be corrugated by subjecting the film to a selected plurality of stretching operations, such as uniaxial stretching operation or biaxial stretching operation. Stretching operations may provide microporous microlayer film with a distinctive porous microlayered morphology, may enhance water vapor transport through the film, and may improve water access, enhance degradability of the film, and enhance elastomeric properties of the film. In a first embodiment, the film is stretched from about 100 to about 1500 percent of its original length. In another embodiment, the film is stretched from about 100 to about 500 percent of its original length.

The parameters during stretching operations include stretching draw ratio, stretching strain rate, and stretching temperature. Stretching temperatures may be in the range of from about 15° C. to about 100° C. In another embodiment, stretching temperatures may be in the range of from about 25° C. to about 85° C. During stretching operation, the multi-microlayer film sample may optionally be heated to provide a desired effectiveness of the stretching.

In one particular aspect of the invention, the draw or stretching system may be constructed and arranged to generate a draw ratio which is not less than about 2 in the machine and/or transverse directions. The draw ratio is the ratio determined by dividing the final stretched length of the microlayer film by the original unstretched length of the microlayer film along the direction of stretching. The draw ratio in the machine direction (MD) should not be less than about 2. In another embodiment, the draw ratio is not less than about 2.5 and in yet another embodiment is not less than about 3.0. In another aspect, the stretching draw ratio in the MD is not more than about 16. In another embodiment, the draw ratio is not more than about 7.

When stretching is arranged in the transverse direction, the stretching draw ratio in the transverse direction (TD) is generally not less than about 2. In another embodiment, the draw ratio in the TD is not less than about 2.5 and in yet another embodiment is not less than about 3.0. In another aspect, the stretching draw ratio in the TD is not more than about 16. In another embodiment, the draw ratio is not more than about 7. In yet another embodiment the draw ratio is not more than about 5.

The biaxial stretching, if used, may be accomplished simultaneously or sequentially. With the sequential, biaxial stretching, the initial stretching may be performed in either the MD or the TD.

The microlayer film of the invention may be pretreated to prepare the film for the subsequent stretching operations. The pretreatment may be done by annealing the film at elevated temperatures, by spraying the film with a surface-active fluid (such as a liquid or vapor from the surface-active material employed to surface-modify the filler material or modify the components of the film), by modifying the physical state of the microlayer film with ultraviolet radiation treatment, an ultrasonic treatment, e-beam treatment, or a high-energy radiation treatment. Pretreatment may also include perforation of the film, generation of z-directional channels of varying size and shapes, penetrating through the film thickness. In addition, the pretreatment of the microlayer film may incorporate a selected combination of two or more of the techniques. A suitable stretching technique is disclosed in U.S. Pat. No. 5,800,758, the disclosure of which is hereby incorporated in its entirety.

The film with corrugated microlayers may be post-treated. The post-treatment may be done by point bonding the film, by calendaring the film, by sealing edges of the film, and by perforation of the film, including generation of channels penetrating through the film thickness.

The microlayer film of this invention may be laminated to one or more nonwoven webs. The nonwoven webs may be spunbond webs, meltblown webs, bonded carded webs, airlaid or wetlaid webs, or other nonwoven webs known in the art.

Accordingly, the microlayer film of this invention is suitable for absorbent personal care items including diapers, adult incontinence products, feminine care absorbent products, training pants, and health care products such as wound dressings. The microlayer film of this invention may also be used to make surgical drapes and surgical gowns and other disposable garments.

Lamination may be accomplished using thermal or adhesive bonding as known in the art. Thermal bonding may be accomplished by, for example, point bonding. The adhesive may be applied by, for example, melt spraying, printing or meltblowing. Various types of adhesives are available including those produced from amorphous polyalphaolefins and ethylene vinyl acetate-based hot melts.

The present invention is further illustrated by the following examples, which are not to be construed in any way as imposing limitations upon the scope thereof. On the contrary, it is to be clearly understood that resort may be had to various other embodiments, modifications, and equivalents thereof which, after reading the description herein, may suggest themselves to those skilled in the art without departing from the spirit of the present invention and/or the scope of the appended claims.

Examples for corrugated microlayer films include films based on polypropylene, and breathable Estane® polyether-type polyurethane elastomer, and breathable Pebax® polyether block polyamide elastomer.

Specific examples include calcium carbonate filled polypropylene H702-35NA. The unfilled polypropylene was purchased from Dow Chemical Company, the business having office in Midland, Mich. The filled polypropylene was microlayered with breathable Estane® 58245 polyurethane elastomer supplied by Novcon, Inc. having an office in Cleveland Ohio 44141. The WVTR of the Estane® 58245 1 mil thick film was measured to be about 8000 g/m$^2$/24 hrs. The multi/microlayer films of 8, 16, and 32 layers were produced. The precursor film thickness (before corrugations) varied from about 1.5 mil to about 12 mil. The ratio of components was: filled PP/Estane®58245 30/70, 50/50, and 70/30. The films with 30/70 and 50/50 component ratio provided films with improved corrugations of layers after stretching in machine direction and heat activation at 80 degrees Celsius.

Other examples include microlayer films of calcium carbonate filled polypropylene H702-35N and Pebax® 2533 elastomer. The Pebax elastomer was purchased from Atofina Chemicals, Inc. having an office in Birdsboro, Pa. 19508. The 16, 32 and 64 layer films were produced with the thickness varying from about 2.5 mil to about 12 mil. The ratio of components was: filled PP/PEBAX® 30/70, 50/50, and 70/30. The films with 30/70 and 50/50 component ratio provided films with improved corrugations of layers after stretching in machine direction and activation at 80 degrees Celcius.

Suitable techniques for obtaining the data for determining the various properties and characteristics of the film are futher described in the Test Procedure section set forth below.

Testing Procedures

Mechanical Properties

A suitable technique for determining the mechanical properties of the film of the invention may employ a MTS Sintech tensile tester (SINTECH 1/D) equipped with the oven attachment and TestWorks 4.05B software. The ASTM test method D 882-97 was used for the evaluation of mechanical properties. A conventional 2.5 in-long "dog-bone" sample was used with the thin section measuring 18 mm long and 3 mm wide. The average thickness of each specimen was entered into the software program prior to testing. The samples were stretched until failure at a rate of 5 inch per minute.

Extensibility and Recovery Properties

The extensibility properties in machine direction were obtained using MTS Sintech tensile tester (SINTECH 1/D) equipped with the oven attachment and TestWorks 4.05B software. Film strips of 3.5 inch in MD and 1 inch in cross direction were used during cyclic tests. The film strips were subjected to three repeated cycles of extension to 100% strain and retraction from extended state at a rate of 250 mm per minute. The extensibility of the film and a retraction of the film from an extended state was analyzed.

Water Vapor Transmission Rate (WVTR)

A suitable technique for determining the WVTR value of a film of the invention is the test procedure standardized by INDA (Association of the Nonwoven Fabrick Industry), number IST-70.4-99. The testing device which may be used for WVTR measurement is known as the Permatran-W Model 100K manufactured by Mocon/Modern Controls, Inc., business having an office in Minneapolis, Minn.

Scanning Electron Microscopy (SEM)

Electron micrographs may be generated by conventional techniques that are well known in the imaging art. In addition, samples may be prepared by employing well known, conventional preparation techniques. For example, the imaging of the cross-section surfaces may be performed with a JEOL 6400 SEM.

Vertical Wicking Analysis 35 millimeter wide film strips may be cut in machine derection or cross direction of the corrugated-microlayer film. The film specimens may be vertically immersed into water for a depth of about 3 millimeters. A height of a vertical water transport by capillary action may be measured in millimeters.

Contact Angle Measurement

The water contact may be measured by recording images of individual, 3-microliter drops using a high speed video system, such as a NAC HSV 1000 motion analysis system. This system is available from Eastman Kodak Company, Motion Analysis Division, a business located in San Diego, Calif. 92121. Strips of the film specimens measuring 6 mm×25 mm (width×length) may be cut from the film samples and taped to a glass slide. The 3-microliter water drops may be set on the surface of the film being tested and video recorded. The quantitative image analyses may be done using suitable image analyses software, such as Concurrent Processing's MAP image analysis software package, which is available from Concurrent Processing Inc., a business having offices in Detroit, Mich. 48214. By analyzing a stop-image of the drop, the left and right contact angles may be measured and the mean values of contact angle may be determined.

EXAMPLES

Example 1

Polypropylene H702-35NA resin was compounded with 20 wt % of CaCO3 filler using the ZSK-30 twin screw extruder. The mean particle size of calcium carbonate was 1 micron. About 2% of hydrophilic surfactant Masil SF19 was intermixed with the pellets of the filled PP resin. The pellets of thermoplastic breathable polyurethane elastomer Estane® 58245, which was dried over night at 50° C., and filled, surfactant-modified polypropylene were fed into the two extruders of the microlayer coextrusion line. The first extruder and volumetric pump temperatures were set at 210° C. for the Estane® resin, and the second extruder and volumetric pump temperatures were set at 185° C. for the filled PP resin. A precursor multilayer film of 16 layers was produced using three multiplier-die elements set at 175° C. The extrusion cast 16-layer films had 70/30 and 50/50 of Estane®/filled-PP ratio. The films were produced with the thickness of about 3 mil, 5 mil and 10 mil. The films were cut into 3 inch by 5 inch strips (5" in machine direction). The strips were stretched from about 350% strain in machine direction (MD) to about 800% strain in MD using tensile tester and environmental chamber set at temperature of 65 degrees Celsius. The film with finer gauge of 3 mil required higher percent of stretch. After releasing the stretching force the films partially recovered stretch length. Relaxed films were heat-activated in the convection oven set at 80° C. An activation time was 15 min. The corrugated-microlayer films were obtained after activation. As a result of relaxation, heat-activation and microlayer corrugations, the films contracted in machine direction from about 60% to about 75% of the stretched length. The thickness of the 70/30 Estane®/filled-PP films with corrugated microlayers dramatically increased to about 30 mils for the 3 mil precursor film and to about 300 mils for the 10 mil precursor film. For the 10 mil thick film, intensive microlayer-corrugations were observed directly after film stretching and relaxation. For the 10 mil and 3 mil precursor films about 2220% and 2100% increase in volume respectively was observed as a result of microlayer corrugations. The increase in volume was measured relative to the volume of uncorrugated precursor films.

Tensile modulus was measured for the 70/30 films in machine direction. The precursor 70/30 films had tensile modulus of about 150 MPa. The film with corrugated microlayers had tensile modulus in machine direction of about 0.3 MPa when normalized to the total thickness of the corrugated microlayer film.

The precursor films of this example as well as corrugated-microlayer films of this example were wettable with a water contact angle of less than 90 degrees. The films with corrugated microlayers of this example demonstrated also high internal wettability of corrugated layers. Fluid transport properties of the corrugated-microlayer films of this example were evaluated by immersing the films in saline solution and water. The films showed rapid fluid movement in cross direction as well as fluid transport in machine direction. In a vertical wicking experiment, water was rapidly conveyed by capillary action in machine direction through the film to the height of up to about 65 millimeters for the film made from the 3 mil thick precursor film. Water was conveyed to the height of about 40 mm for the film made from 5 mil thick precursor film, and water was conveyed to the height of about 30 mm for the film made from the 10 mil thick precursor film. This example showed that the film capillary suction may be reduced by increasing the film thickness. The films of this example showed also high capacity to absorb fluids.

Example 2

A 10 mil thick 16 layer Pebax®92533/(Polypropylene+30% $CaCO_3$) 70/30 precursor film was produced using the technique and PP resin of Example 1. A surfactant treatment was not used in this example. The film strips were stretched in machine direction at 65° C. to about 1000% strain. The stretched film samples were activated at 80 degrees Celsius for about 15 min. Intensive microlayer corrugations were observed in the activated film. The film increased in thickness while recovering in machine direction about 60% of its length. Extensibility in machine direction of the corrugated-microlayer film of this example was evaluated using extension cycle experiments with up to 100% strain. The films demonstrated extensibility of up to 100% elongation and a significant retraction to about its original length when the extension force was removed.

Example 3

A 64 layer Pebax®2533/(polypropylene+30% $CaCO_3$) 70/30 precursor film was produced using five multiplier-die elements and the technique, and polypropylene resin of Example 1. A surfactant treatment was not used in this example. Film thickness was 5 mil and 10 mil. The film strips were stretched in machine direction at 65° C. to about 1000% strain. The stretched film samples were activated at 80 degrees Celsius for about 15 min. An intensive microlayer corrugations have not been observed for this 64 layer film. This example demonstrates that for a given film thickness an ability to form a film with corrugated microlayers decreases with increasing number of layers as a result of improved apparent adhesion between the microlayers.

Example 4

Estane®58245/(polypropylene+20% $CaCO_3$) 70/30 16layer films with a thickness of 5 mil and 10 mil were produced using the procedures of Example 1. A surfactant treatment was not used in this example. The film strips of 1 inch wide were stretched at 65° C. to up to 900% for 5 mil film and 800% for the 10 mil film using tensile tester with a stretching gauge corresponding to grips separation distance of 1 inch. Stretching speed of 5 inch/min was used, however, higher stretching speed of up to 80 inch/min was also tested. After stretching force was released, the film strips have recovery of about 26% of the stretched length. After activation at 80° C. the films formed microlayer corrugations with the PP-layer corrugations formed in the machine direction and Estane®-layer corrugations formed in the cross direction. After activation the film-strips became thick, puffy and extremely soft. Thickness was increased to about 60 mil for the 5 mil film and to about 200–300 mils for the 10 mil film. The 5 mil thick film required more stretch to achieve uniform microlayer corrugations compared to 10 mil thick films. For example, the minimum stretch required for 5 mil and 10 mil films was 800% and 500% respectively. The 5 mil films formed finer microlayer corrugations compared to 10 mil films were layer corrugations were more coarse. Some of 5-mil and 10-mil film specimens were perforated prior to stretching. A die with a diamond pattern containing 32 pins/inch$^2$ was used for the perforation. The perforated and unperforated samples tended to have similar recoveries after stretch. The perforated specimens required less stretch than unperforated specimens to produce microlayer corrugations; the unperforated and perforated 3 inch wide 10 mil thick strips stretched at 65° C. required a 500% and a 400% strain respectively to form the microlayer corrugations after activation at 80° C.

Example 5

5-mil and 10-mil thick Morthane® PN3429/(PP+20% $CaCO_3$) 70/30 16-layer films were produced using the procedures of Example 1. The film strips were stretched to up to 1300% strain at 65° C. The recovery was similar for the 2 film thicknesses—the 5-mil and 10-mil film 1 in strips stretched to 1300% strain had a recovery of 63.2% and 65.2%, respectively after the stretching force was released. These films did not appear to have uniform microlayer-corrugations after activation at 85° C., at least under the conditions studied. The films tended to produce gathered, ruffled specimens with lengthwise stripes of different shrinkage levels and limited delamination and corrugation. The results were more promising with the 10-mil film, with some larger areas of corrugations.

Example 6

5-mil and 10-mil thick Pebax®2533/(PP+30% $CaCO_3$) 70/30 16-layer films were stretched at 25° C., 65° C., 85° C. and 95° C. At 25° C., the 10-mil film was stretched to up to 1600% strain and at 65° C., the 5-mil and 10-mil films were both stretched to up to 1300% strain. At 85° C., the 10-mil film was stretched to up to 800% strain. At 95° C., the 5-mil film was stretched to up to 1300% strain and the 10-mil film was stretched to up to 600% strain. The latent deformation and the recovery tended to increase as the stretch temperature was increased. The 10-mil film 1 in strips stretched to 600% strain at 65° C., 85° C., and 95° C. had a recovery of about 50%, 72%, and 73%, respectively. The recovery appeared to be similar for the 5-mil and 10-mil films. Microlayer-corrugations were achieved with both film thicknesses at all the stretch temperatures using activation temperatures of 80° C. or 15° C. higher than the stretch temperature for 85° C. and 95° C. stretch. After activation, the film strips became thick with the thickness ranging from 40 mil to about 300 mil, puffy, and soft. SEM examination revealed that both the Pebax® and the PP layers had corrugated, with the PP-layer corrugations formed in the machine direction and the Pebax®-layer corrugations formed in the cross direction. A minimum stretch was required to achieve uniform results throughout the film gage—stretching further was usually possible and often produced thicker, fluffier samples. Increasing the stretch temperature decreased the stretch necessary to achieve uniform microlayer corrugations. The 5-mil film generally required more stretch than the 10-mil film to produce corrugated microlayers; the 5-mil and 10-mil strips stretched at 65° C. required a 1300% and an 1100% strain stretch, respectively. Some 10-mil specimens were perforated prior to stretching at 65° C. A die with a diamond pattern containing 32 pins/inch$^2$ was used for the perforation. The pins diameter was about 1 millimeter. The microlayer-corrugations were more orderly and uniform across the perforated-film samples. The perforated specimens required less stretch than unperforated specimens to produce microlayer corrugations; the unperforated and perforated 3 inch wide 10-mil thick strips stretched at 65° C. required an 1100–1200% and a 700–800% strain stretch respectively to form the corrugated microlayers.

I claim:

1. A drapable, wettable, multi-microlayer film comprising a plurality of coextruded microlayers including at least a first corrugated microlayer of a polymer having a first recovery percentage and at least a second corrugated microlayer of a polymer having a second recovery percentage, wherein the first corrugated microlayer defines a first set of channels and the second corrugated microlayer defines a second set of channels aligned substantially perpendicular to the first set of channels and wherein the second corrugated microlayer is partially delaminated from the first corrugated microlayer.

2. The multi-microlayer film of claim 1, wherein the polymer having a first recovery percentage comprises a thermoplastic elastomer.

3. The multi-microlayer film of claim 2, wherein the thermoplastic elastomer is selected from metallocene polyolefins, single-site catalyzed olefinic elastomers, thermoplastic polyester or polyether polyurethanes, EVA copolymers, polyether block polyamide copolymers, ether-ester segmented-block elastomers, styrenic block copolymers, blends and mixtures thereof.

4. The multi-microlayer film of claim 3, wherein the thermoplastic elastomer is a polyether thermoplastic polyurethane.

5. The multi-microlayer film of claim 1, wherein the polymer having a second recovery percentage comprises a thermoplastic stretchable polymer.

6. The multi-microlayer film of claim 5, wherein the thermoplastic stretchable polymer is selected from polycaprolactone, polymers and copolymers of polylactic acid, polymers and copolymers of polybutylene succinate, poly (butylene succinateadipate), polyesters, polypropylene, copolymers of polypropylene, polyethylene, copolymers of polyethylene, blends and mixtures thereof.

7. The multi-microlayer film of claim 6, wherein the thermoplastic stretchable polymer is polypropylene.

8. The multi-microlayer film of claim 1, wherein the corrugated microlayers further comprise an additional material selected from a filler material, a surfactant, a blowing agent and mixtures thereof.

9. The multi-microlayer film of claim 8, wherein the filler material is a particulate material selected from metal oxides, metal hydroxides, metal carbonates, metal sulfates, calcium carbonate, clay, alumina, titanium dioxide, rubber powder, rubber emulsions, pulp powder, wood powder, chitozan powder, polyacrylic acid powder, and mixtures thereof.

10. The multi-microlayer film of claim 1, wherein the microlayer of a polymer having a first recovery percentage further comprises an additional material selected from a filler material, a surfactant, a blowing agent and mixtures thereof.

11. The multi-microlayer film of claim 10, wherein the filler material is a particulate material selected from metal oxides, metal hydroxides, metal carbonates, metal sulfates, calcium carbonate, clay, alumina, titanium dioxide, rubber powder, rubber emulsions, pulp powder, wood powder, chitozan powder, polyacrylic acid powder, and mixtures thereof.

12. The multi-microlayer film of claim 1, wherein each microlayer has a thickness of from about 0.1 microns to about 150 microns.

13. The multi-microlayer film of claim 12, wherein each microlayer has a thickness of from about 0.5 microns to about 100 microns.

14. The muti-microlayer film of claim 1, wherein the multi-microlayer film has a thickness of from about 3 mil to about 1000 mil.

15. The multi-microlayer film of claim 14, wherein the multi-microlayer film has a thickness of from about 10 mil to about 500 mil.

16. The multi-microlayer film of claim 1, wherein the multi-microlayer film comprises from about 5 to about 100 microlayers.

17. The multi-microlayer film of claim 16, wherein the multi-microlayer film comprises from about 16 to about 60 microlayers.

18. The multi-microlayer film of claim 1, further comprising a third polymer microlayer between and partially laminated to the first corrugated microlayer and the second corrugated microlayer, the third polymer layer comprising a melt-extrudable polymer.

19. The multi-microlayer film of claim 18, wherein the third polymer is selected from polyolefins, thermoplastic polyesters, polyalkane-poly(ethylene oxide) block copolymers, filled polyester resins, polyethers, block copolymers of polyesters and polyethers, polyolefin block copolymers, ethylene vinyl acetate copolymers, thermoplastic water soluble polymers, thermoplastic swellable polymers, superabsorbent materials; blends and mixtures thereof.

20. The multi-microlayer film of claim 1, wherein the multi-microlayer film has a tensile modulus in a machine direction of from about 0.2 Mpa to about 20 Mpa.

21. The multi-microlayer film of claim 20, wherein the multi-microlayer film has a tensile modulus in a machine direction of from about 0.5 Mpa to about 5 Mpa.

22. The multi-microlayer film of claim 1, wherein the multi-microlayer film has been pre-stretched from about 100 to about 1500 percent of the film's original length.

23. The multi-microlayer film of claim 1, wherein the multi-microlayer film has an increase in void volume of from about 500% to about 5000% relative to the volume of the precursor unstretched film.

24. The multi-microlayer film of claim 23, wherein the multi-microlayer film has an increase in void volume of from about 1000% to about 3000% relative to the volume of the precursor unstretched film.

25. The multi-microlayer film of claim 1, wherein the multi-microlayer film has a breathability of from about 500 g mil/day/m$^2$ to about 25,000 g mil/day/m$^2$.

26. The multi-microlayer film of claim 25, wherein the multi-microlayer film has a breathability of from about 1000 g mil/day/m$^2$ to about 20,000 g mil/day/m$^2$.

27. The multi-microlayer film of claim 1, wherein the multi-microlayer film has a bulk density of less than about 0.5 grams per cubic centimeter.

28. The multi-microlayer film of claim 27, wherein the multi-microlayer film has a bulk density of less than about 0.1 grams per cubic centimeter.

29. The multi-microlayer film of claim 28, wherein the multi-microlayer film has a bulk density of less than about 0.05 grams per cubic centimeter.

30. The multi-microlayer film of claim 29, wherein the multi-microlayer film has a bulk density of less than about 0.03 grams per cubic centimeter.

31. The multi-microlayer film of claim 1, wherein the multi-microlayer film has a vertical wicking of from about 10 mm to about 200 millimeters.

32. The multi-microlayer film of claim 31, wherein the multi-microlayer film has a vertical wicking of from about 20 mm to about 150 millimeters.

33. The multi-microlayer film of claim 32, wherein the multi-microlayer film has a vertical wicking of from about 40 mm to about 100 millimeters.

34. A personal care item comprising a body of absorbent material and a microlayer polymer film of claim 1 attached to the body of absorbent material.

35. The personal care item of claim 34, wherein the personal care item is selected from a diaper, an adult incontinence product, a feminine care absorbent product, or a training pant.

36. A laminate comprising a microlayer film of claim 1 laminated to one or more non-woven webs.

37. An absorbent disposable article comprising a microlayer film of claim 1.

* * * * *